United States Patent
Servell et al.

(10) Patent No.: US 9,439,731 B2
(45) Date of Patent: Sep. 13, 2016

(54) METHODS FOR RESHAPING CARTILAGE STRUCTURES

(71) Applicant: Chondrocyte LLC, Henderson, NV (US)

(72) Inventors: Pascal Servell, Dallas, TX (US); Jack Savage, Sandy, UT (US); Shilo C. Case, Sandy, UT (US); Gregg D. Niven, Kaysville, UT (US)

(73) Assignee: Chondrocyte, LLC, Henderson, NV (US)

( * ) Notice: Subject to any disclaimer, the term of this patent is extended or adjusted under 35 U.S.C. 154(b) by 318 days.

(21) Appl. No.: 14/120,426

(22) Filed: May 28, 2013

(65) Prior Publication Data
US 2015/0018814 A1    Jan. 15, 2015

(51) Int. Cl.
*A61B 19/00*    (2006.01)
*A61B 18/20*    (2006.01)
*A61B 18/00*    (2006.01)

(52) U.S. Cl.
CPC .... *A61B 18/203* (2013.01); *A61B 2018/00321* (2013.01)

(58) Field of Classification Search
CPC .......... A61N 5/06; A61N 2005/0642; A61N 2005/0643; A61N 2005/067; A61N 1/36032; A61B 18/18; A61B 18/20; A61B 18/203; A61B 2018/1807; A61F 2/18; A61F 2/18186; A61F 2002/183
USPC ........ 607/88, 89, 96, 108, 109; 606/3, 9–12; 623/10; 128/898
See application file for complete search history.

(56) References Cited

U.S. PATENT DOCUMENTS

| | | | |
|---|---|---|---|
| 4,187,838 A | 2/1980 | Dubrowski | |
| 4,850,055 A | 7/1989 | Hwang | |
| 5,295,950 A | 3/1994 | Godley | |
| 5,775,336 A | 7/1998 | Morris | |
| 6,517,557 B1 * | 2/2003 | Sorribes | A61F 11/00 606/1 |
| 6,626,945 B2 | 9/2003 | Simon et al. | |
| 6,632,246 B1 | 10/2003 | Simon et al. | |
| 6,852,125 B2 | 2/2005 | Simon et al. | |
| 7,025,061 B2 | 4/2006 | Haussmann | |
| 7,069,745 B1 | 7/2006 | Finley | |
| 7,093,600 B2 | 8/2006 | Sorribes | |

(Continued)

FOREIGN PATENT DOCUMENTS

| | | |
|---|---|---|
| CA | 1078690 | 6/1980 |
| JP | 10014971 | 1/1998 |

(Continued)

OTHER PUBLICATIONS

Leclere et al. , Laser-Assisted Cartilage Reshaping for Protruding Ears: A Review of the Clinical Applications, Laryngoscope, 125:2067-2071, 2015.

(Continued)

*Primary Examiner* — Ahmed Farah
(74) *Attorney, Agent, or Firm* — Brian C Trask

(57) ABSTRACT

Described are methods and systems for reshaping a cartilage structure. Such methods comprise treating the cartilage structure with electromagnetic energy and fitting a device to the cartilage structure to retain it in the desired place, form, and/or orientation. Systems comprise an emitter of electromagnetic energy and a device to the cartilage structure to retain it in the desired place, form, and/or orientation.

11 Claims, 1 Drawing Sheet

(56) References Cited

U.S. PATENT DOCUMENTS

| | | | |
|---|---|---|---|
| 7,117,546 | B2 | 10/2006 | Goulding |
| 7,153,313 | B2 | 12/2006 | Whitton |
| 7,850,702 | B2 | 12/2010 | Sorribes et al. |
| 8,113,208 | B2 | 2/2012 | Chaisson et al. |
| 8,491,510 | B2 | 7/2013 | Byrd et al. |
| 8,627,824 | B2 | 1/2014 | Koehler |
| 8,715,347 | B2 * | 5/2014 | Servell .................. A61B 5/1079 606/204.15 |
| 9,173,762 | B2 | 11/2015 | Case et al. |
| 2001/0039455 | A1 | 11/2001 | Simon et al. |
| 2004/0039447 | A1 | 2/2004 | Simon et al. |
| 2004/0162622 | A1 | 8/2004 | Simon et al. |
| 2006/0042640 | A1 | 3/2006 | Haussmann |
| 2008/0071255 | A1 * | 3/2008 | Barthe .................. A61B 8/08 606/9 |
| 2008/0154250 | A1 * | 6/2008 | Makower .............. A61B 17/24 606/10 |
| 2008/0195216 | A1 | 8/2008 | Philipp |
| 2008/0269674 | A1 * | 10/2008 | Stone ................. A61B 17/1635 604/80 |
| 2009/0030358 | A1 | 1/2009 | Byrd et al. |
| 2010/0087898 | A1 * | 4/2010 | Clement ............. A61N 5/0616 607/88 |
| 2010/0204793 | A1 * | 8/2010 | Byrd ................... A61B 19/24 623/10 |
| 2011/0266265 | A1 | 11/2011 | Lang |
| 2012/0191005 | A1 * | 7/2012 | Sobol ................. A61B 18/20 600/562 |
| 2012/0226307 | A1 | 9/2012 | Servell et al. |
| 2012/0323227 | A1 * | 12/2012 | Wolf ................. A61B 18/1485 606/2 |
| 2014/0188158 | A1 * | 7/2014 | Servell ................. A61B 5/1079 606/204.15 |
| 2015/0018814 | A1 | 1/2015 | Servell et al. |

FOREIGN PATENT DOCUMENTS

| | | |
|---|---|---|
| JP | 4431066 | 3/2010 |
| WO | 0191672 | 12/2001 |
| WO | 2009014908 | 1/2009 |
| WO | 2011/129900 | 10/2011 |
| WO | 2013/142342 | 9/2013 |

OTHER PUBLICATIONS

N. Ignatieva, et al., Molecular processing and structural alterations in laser reshaping of cartilage, Article in Laser Physics letters, Oct. 2007.

Leclere et al., Cartilage reshaping for protruding ears: A perspective long term follow-up of 32 procueduers, Lasers in Surgery and Medicine 43:875-880 (2011).

Trellos, et al., Correction of ear malformations by laser-assisted cartilage reshaping (LACR), Lasers in Surgery and Medicine 38:659-662 (2006).

Mordon et al., Laser cartilage reshaping in an in Vivo Rabbit model using a 1.54 (micro)m Er:Glass laser, Lasers in Surgery and Medicine 34:315-322 (2004).

Leclere et al., Laser-Assisted Septal Cartilage Reshaping (LASCR): A prospective study in 12 patients, Lasers in Surgery and Medicine 42:693-698 (2010).

Extended European Search Report and Written Opinion, PCT/US2011000688, P99789EP00, mailed Feb. 26, 2015.

Auri Clinic, website printout, 1 page, http://shop.auriclinic.com/index.php?language=en, visited Oct. 29, 2009.

Earwell TM Infant Ear Correction System, Brochure, Becan Medical Limited, Tucson, Arizona, 2008.

Leclere et al., Laser-Assisted Cartilage Reshaping (LACR) for Treating Ear Protrusions: A Clinical Study in 24 Patients, Aesth Plast Surg. May 30, 2009, published online by Springer.

Mordon et al., Laser Cartilage Reshaping in an in Vivo Rabbit Model Using a 1.54 f.!m Er:Giass Laser, Lasers Surg. Med. 2004, pp. 315-322, vol. 34.

Mordon et al., Correction of ear malformations by Laser Assisted Cartilage reshaping (LACR): a preliminary study in 10 patients, Lasers Surg. Med. 2006, pp. 659-662, vol. 38 No. 7.

PCT International Search Report and Written Opinion, PCT/US2013/032182 dated Jul. 10, 2013.

PCT International Search Report and Written Opinion, PCTUS2011/000688 dated Jan. 17, 2012.

Sorribes, et al., Nonsurgical Treatment of Prominent Ears With the Auri Method, 2002, pp. 1369-1376, vol. 28.

Keefe MW, Rasouli A, Telenkov SA, et al. Radiofrequency cartilage reshaping: efficacy, biophysical measurements, and tissue viability. Arch Facial Plast Surg 2003;5:46-52.

* cited by examiner

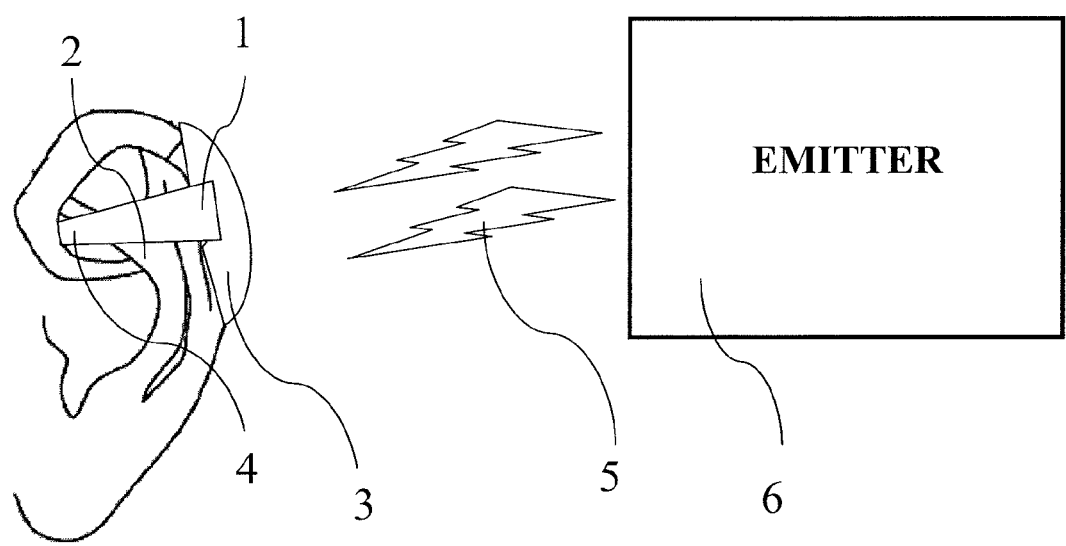

METHODS FOR RESHAPING CARTILAGE STRUCTURES

TECHNICAL FIELD

The invention relates to systems and methods for reshaping cartilage structures, such as a human or mammalian ear, for example as a cosmetic treatment.

BACKGROUND

Ear deformations affect 5% of the Caucasian and Latino population or 12.1 million people (5% of 242.3 million). Each year, 4.26 million children are born of white or Latino parents (2.3 million whites and 1 million Hispanics). Of these, approximately 165,000 are born with deformed ears.

However, according to the American Society of Plastic Surgeons (ASPS), only 29,434 cosmetic ear surgery procedures were performed in 2009 in the US and these were primarily performed on children, leaving the vast majority of the population untreated (it is interesting to note that otoplasty is the only cosmetic procedure performed on children, testifying to the damaging psychological issues stemming from this condition).

The average child has 85% ear development by 3 years of age and ears are typically fully grown by the age of 7 years (the height continues to grow into adulthood, but the width and distance from ear to scalp changes little). This fact in part explains why this procedure is popular with children, as procedures performed from this age onwards will yield permanent results.

All ears also have surprisingly similar features in terms of size, protrusion from the scalp and angle from the cranium. The following is a list of considered standard sizes: fully grown ears protrude from the scalp about 1.8-2.0 cm at midpoint; ear length is typically 5.5-6.5 cm; ear width is typically 3.0-4.5 cm; the ratio between width and length is about 50% to 60%; helical Rim (Helix) 7 mm or about 10% of the height; ear vertical axis 15 to 30 degrees posterior (with the top further back than the bottom).

Features constituting what is considered "normal" ear features are: scapha angle greater than 90 degrees; conchal bowl height less than 1.5 cm; and angle head to ear: female less than 21 degrees and male less than 25 degrees.

Ear deformations typically fall into two broad categories, cartilage deformations and non-cartilage related deformations. Cartilage deformations include prominent (or bat) ears which typically is a problem either of an oversized concha, or too wide an antihelical fold angle or a combination of the two; helical deformations that include: constricted ear including hooding or folding of the helical rim; lop ear where the top of the ear is folded down and forward; cup ear including malformed protruding ear with the top folded down and a large concha; shell ear where curve of the outer rim as well as the folds and creases are missing; and stahl's ear (Spock's ear) where there is an extra fold and pointed top. Non-cartilage related deformations include: lobe deformations, macrotia (oversized ears), and microtia (undersized ears).

Surgical Ear Correction: Otoplasty

The first otoplastic technique to correct protruding ears is attributed to Ely in 1881. Since that report, over 180 surgical techniques have been described in the literature for the correction of protruding ears. These techniques can be subdivided into 3 sub-groups:

"Suture only" technique: First described by Furnas in 1968 (and still used to this day), this technique is used primarily to set back the ears and involves retracting the skin behind the ear and place 2-3 non-resorbable sutures to retract the position of the ear. The Mustarde method is today the most common.

Cartilage splitting or weakening technique or "Davis" method: Excision of skin and cartilage to correct conchal hypertrophy.

Combination of the above two or "converse Wood-Smith" technique: uses a cartilage cutting and suture method to correct and create an anti-helical fold.

All these surgical techniques tend to be performed on an outpatient basis under sedation, although when dealing with children it is advisable to perform it under general anesthesia. The procedure is generally performed primarily by Facial Plastic Surgeons and, to a lesser extent by Dermatologists, ENT and Maxillofacial Surgeons. It typically takes 2 to 3 hours to perform and is not without risks.

Major complications from corrective ear surgery may occur and can be divided into two categories: immediate complications: hematoma and infection that may result in necrosis; and long-term complications include hypertrophic (keloid) scars, loss of sensitivity (resulting from damage to nerve endings), skin and cartilage necrosis as well as unaesthetic results or recurrence of the ear deformity. These complications are responsible for the high (10%) rate of repeat surgeries.

BRIEF SUMMARY

Described herein are methods and systems for shaping or reshaping a cartilage structure, the method comprising treating the cartilage structure of a subject with electromagnetic energy of from 50 to 1200 nm or 2100 of from 250 to 1315 nm, 1325 to 1445 nm or 1455 to 1535 nm or 1540 at 11 $J/cm^2$ or less, or 1540 at 13 $J/cm^2$ or higher, 1545 to 2095 or 2105 to 10600 nm wavelength; and fitting the treated cartilage structure with a device designed to retain the cartilage structure in a desired orientation, shape, and/or location.

Also described herein are methods and systems for shaping or reshaping a cartilage structure, the method comprising treating the cartilage structure of a subject with electromagnetic energy of from 1 KHz to 200 MHz; and fitting the treated cartilage structure with a device designed to retain the cartilage structure in a desired orientation, shape, and/or location.

Further described herein are methods and systems for shaping or reshaping a cartilage structure, the method comprising treating the cartilage structure of a subject with a total fluence of from 1 to 60 or from 90 to 100 Joules of electromagnetic energy per unit area; and fitting the treated cartilage structure with a device designed to retain the cartilage structure in a desired orientation, shape, and/or location.

Additionally, described herein are methods and systems for shaping or reshaping a cartilage structure, the method comprising exposing the cartilage structure, or the area surrounding a cartilage structure, of a subject to trauma; and fitting the treated cartilage structure with a device designed to retain the cartilage structure in a desired orientation, shape, and/or location.

BRIEF DESCRIPTION OF THE DRAWINGS

FIG. 1 is a depiction of one embodiment of system including an emitter and a device designed to retain the cartilage structure in a desired orientation, shape, and/or location.

DETAILED DESCRIPTION OF THE INVENTION

Embodiments include methods and systems for forming or reforming cartilage structures in a subject. The forming or reforming of cartilage structures may take place through the process of chondrogenesis. The cartilage structures may be any cartilage-containing portion of a subject including, but not limited to, the joints between bones, the rib cage, the ear, the nose, the elbow, the knee, the ankle, the bronchial tubes, the intervertebral discs, and nasal septum. One example of such a method comprises treating a cartilage structure with a laser so as to stimulate chondrogenesis as described by Leclere et al. (Aesth. Plast. Surg. April 2010; 34(2):141-6); Mordon et al. (Lasers Surg. Med. 2004 34:315-322) and Mordon et al. (Lasers Surg. Med. August 2006; 38(7):659-62) the contents of the entirety of each of which are incorporated herein by reference.

Electromagnetic energy may be applied to the cartilage structure in order to stimulate reformation of the cartilage structure. Before, during, or after the application of the electromagnetic energy, the cartilage structure may be fitted with a device designed to retain the cartilage structure in the orientation, shape, and/or location desired after the reforming of the cartilage structure. Examples of such devices include, but are not limited to, those described in U.S. patent applications Ser. Nos. 13/498,573 and 61/613,358, WO 2011/129900 (filed Oct. 20, 2011), and PCT/US2013/032182, (filed Mar. 15, 2013) the contents of the entirety of each of which are incorporated herein by reference.

A device designed to retain the cartilage structure in the orientation, shape, and/or location desired may be of the form depicted in FIG. 1. A shown therein, a device may comprise a ear device (1) fitting over the helix of the outer ear and a projection (2) originating and attached to the ear device (1) at its proximal end (3) and extending across the anti-helix and the distal end (4) fitting into the scapha under the helix at about the lower ems of the anti-helix and/or the fossa trangularis. The projection (2) and ear device (1) may be formed as a single piece or multiple pieces.

The electromagnetic energy (5) may be applied to the cartilage structure in the form of laser light, e.g., via an emitter (6). The laser light may be from about 450 to about 10600 nm in wavelength or from 450 to 10600 nm in wavelength. The laser light may be from about 250 to 1315 nm, 1325 to 1445 nm or 1455 to 1535 nm or 1540 at 11 J/cm$^2$ or less, or 1540 at 13 J/cm$^2$ or higher, 1545 to 2095 or 2105 to 10600 nm wavelength. In particular, the laser light may specifically exclude wavelengths of 1320 nm, 1450 nm, 1540 nm at 12 J/cm$^2$, or 2100 nm. The laser light may be, e.g., 450, 500, 550, 600, 650 700, 750, 800, 850, 900, 950, 1000, 1100, 1200, 1300, 1400, 1500, 1600, 1700, 1800, 1900, 2000, 2050, 2150, 2200, 2300, 2400, 2500, 2600, 2700, 2800, 2900, 3000, 4000, 5000, 6000, 7000, 8000, 9000, 10000, 10100, 10200, 10300, 10400, 10500, 10600, or more nm in wavelength.

The laser emitter may be calibrated and/or independently determined to emit the desired wavelength before use. Before application of the laser to the cartilage structure, the wavelength of the laser light being emitted may be determined. Determination of the wavelength, calibration of the laser wavelength, and/or independent determination may be carried out using equipment and procedures well known to those of ordinary skill in the art of lasers. For example, the power meters, energy sensors, and beam profilers available from Ophir-Spiricon LLC (North Logan, Utah, USA) may be used to determine the wavelength, or calibrate the laser Once the wavelength emitted has been determined, the laser may be calibrated to emit a wavelength as desired above. The laser may be calibrated to vary from a chosen wavelength by no more than, e.g., 1%, 0.1%, 0.01%, 0.001%, 0.0001%, or 0.00001%. Instead of calibrating the laser, the total fluence of energy applied, the number of pulses, and/or the pulse length may be altered to compensate for the actual wavelength emitted.

As depicted in FIG. 1, a system may comprise a laser emitter (6) that emits laser light (5) as identified above and a device (e.g. (1)-(4)) designed to retain the cartilage structure in the orientation, shape, and/or location desired. The tip of the laser may incorporate an integrated cooling device such that when in use, the cooled tip of the device imparts a cooling effect on any tissue or cartilage structure being irradiated by the laser. One non-limiting example of such a cooling tip is the Koolburst, available from Quantel Deima GmbH, Erlangen Germany utilizing the manufacturer's instructions.

The electromagnetic energy may be applied to the cartilage structure in the form of lower power waves. The lower power waves may be from about 1000 Hz to about 50 MHz or from 1000 Hz to 50 MHz. The lower power waves may be from about 300 KHz to about 200 MHz or from 300 KHz to 200 MHz.

The lower power wave emitter may be calibrated and/or independently determined to emit the desired Hz before use. Before application of the laser to the cartilage structure, the Hz of the electromagnetic energy being emitted may be determined. Determination of the Hz, calibration of the emitter, and/or independent determination may be carried out using equipment and procedures well known to those of ordinary skill in the art. For example, the power meters, energy sensors, and beam profilers available from Ophir-Spiricon LLC (North Logan, Utah, USA) may be used to determine the Hz and/or calibrate the emitter.

Once the Hz emitted has been determined, the emitter may be calibrated to emit a wavelength as desired above. The emitter may be calibrated to vary from a chosen Hz by no more than, e.g., 1%, 0.1%, 0.01%, 0.001%, 0.0001%, or 0.00001%. Instead of calibrating the emitter, the total fluence of energy applied, the number of pulses, and/or the pulse length may be altered to compensate for the actual Hz emitted.

A system may comprise a lower power wave emitter that emits electromagnetic energy as identified above and a device designed to retain the cartilage structure in the orientation, shape, and/or location desired.

One or more pulses or electromagnetic energy may be applied to a particular area of the cartilage structure in an individual treatment. The number of pulses to a particular cartilage area may be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more. The number of pulses may be between 1 and 50. In particular, 7 pulses may be specifically excluded.

The pulse length of the application of the electromagnetic energy may be varied. The pulse length may be from 1 nanosecond to 1 second. Further, the pulse length may be from 1 microsecond to 500 milliseconds. The pulse length may be, e.g., 1, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 nanoseconds. Further, the pulse length may be, e.g., 10, 20, 30, 40, 50, 60, 70, 80, 90, 100, 150, 200, 250, 300, 350, 400, 450, 500, or more milliseconds.

The electromagnetic energy emitter may be calibrated and/or independently determined to emit the pulse length before use. Before application of the electromagnetic energy to the cartilage structure, the pulse length of the electromagnetic energy being emitted may be determined. Determination of the pulse length, calibration of the emitter, and/or independent determination may be carried out using equipment and procedures well known to those of ordinary skill in the art. For example, the power meters, energy sensors, and beam profilers available from Ophir-Spiricon LLC (North Logan, Utah, USA) may be used to determine the pulse length and/or calibrate the emitter.

Once the pulse length emitted has been determined, the emitter may be calibrated to emit a pulse length as desired above. The emitter may be calibrated to vary from a chosen pulse length by no more than, e.g., 1%, 0.1%, 0.01%, 0.001%, 0.0001%, or 0.00001%. Instead of calibrating the emitter, the total fluence of energy applied, the number of pulses, and/or the wavelength of the electromagnetic energy may be altered to compensate for the actual pulse length emitted.

A system may comprise an electromagnetic energy emitter that emits electromagnetic energy in pulses of the desired length as identified above and a device designed to retain the cartilage structure in the orientation, shape, and/or location desired. The electromagnetic energy emitter may be calibrated and/or independently determined to emit pulses of the desired length.

Where multiple pulses are used, the interval between pulses may be varied. The interval length may be from 1 nanosecond to 1 second. Further, the interval length may be from 1 microsecond to 500 milliseconds. The interval length may be, e.g., 1, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 nanoseconds. Further, the interval length may be, e.g., 10, 20, 30, 40, 50, 60, 70, 80, 90, 100, 150, 200, 250, 300, 350, 400, 450, 500, or more milliseconds. The electromagnetic energy emitter may be calibrated and/or independently determined to emit pulses at an interval of the desired length before use.

A system may comprise an electromagnetic energy emitter that emits electromagnetic energy in pulses at an interval of the desired length as identified above and a device designed to retain the cartilage structure in the orientation, shape, and/or location desired. The electromagnetic energy emitter may be calibrated and/or independently determined to emit pulses at an interval of the desired length.

The amount of electromagnetic energy delivered per pulse may vary. For example, a pulse may apply, e.g., 0.01, 0.02, 0.03, 0.04, 0.05, 0.06, 0.07 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more Joules per pulse. The amount of electromagnetic energy may be from about 0.1 to about 30 Joules per pulse or from 0.1 to 30 Joules per pulse. Further, the amount of electromagnetic energy may be from about 0.1 to about 10 Joules per pulse or from 0.1 to 10 Joules per pulse. In particular, energy values of 0.1, 0.2, 0.3, 0.4, 2, 12, and 14 Joules per pulse may be specifically excluded.

The electromagnetic energy emitter may be calibrated and/or independently determined to emit the chosen Joules/pulse before use. Before application of the electromagnetic energy to the cartilage structure, the Joules/pulse emitted may be determined. Determination of the Joules/pulse, calibration of the emitter, and/or independent determination may be carried out using equipment and procedures well known to those of ordinary skill in the art. For example, the power meters, energy sensors, and beam profilers available from Ophir-Spiricon LLC (North Logan, Utah, USA) may be used to determine the Joules/pulse and/or calibrate the emitter.

Once the Joules/pulse emitted has been determined, the emitter may be calibrated to emit a Joules/pulse as desired above. The emitter may be calibrated to vary from a chosen Joules/pulse by no more than, e.g., 1%, 0.1%, 0.01%, 0.001%, 0.0001%, or 0.00001%. Instead of calibrating the emitter, the total fluence of energy applied, the number of pulses, and/or the wavelength of the electromagnetic energy may be altered to compensate for the actual Joules/pulse emitted.

A system may comprise an electromagnetic energy emitter that emits electromagnetic energy at a desired Joules/pulse as identified above and a device designed to retain the cartilage structure in the orientation, shape, and/or location desired. The electromagnetic energy emitter may be calibrated and/or independently determined to emit the desired Joules/pulse.

The cumulative electromagnetic energy delivered to a unit area may vary. The cumulative electromagnetic energy delivered is the sum of the energy delivered by one or more pulses to a particular area. The cumulative electromagnetic energy may be, e.g., 1, 5, 10, 15 20, 25, 30, 35, 40, 45, 50, 55, 60, 61, 62, 63, 64, 65, 66, 67, 68, 69, 70, 71, 72, 73, 74, 75, 76, 77, 78, 79 80, 81, 82, 83 84, 85, 86 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900, 1000 or more Joules per unit area. The cumulative electromagnetic energy delivered to a particular area may be from about 50 to about 100 Joules or from 50 to 100 Joules. For example, the cumulative electromagnetic energy delivered to a particular area may be from about 60 to about 90 Joules or from 60 to 90 Joules. For example, the cumulative electromagnetic energy delivered to a particular area may be from about 65 to about 75 Joules or from 65 to 75 Joules. The cumulative electromagnetic energy delivered to a particular area may be from about 1 to about 60 Joules or from 1 to 60 Joules. The cumulative electromagnetic energy delivered to a particular area may be from about 90 to about 150 Joules or from 90 to 150 Joules. The cumulative electromagnetic may specifically exclude 70 or 84 Joules. The electromagnetic energy emitter may be calibrated and/or independently determined to emit the desired amount of Joules per single/or cumulative pulses before use.

The electromagnetic energy emitter may be calibrated and/or independently determined to emit the chosen cumulative electromagnetic energy before use. Before application of the electromagnetic energy to the cartilage structure, the cumulative electromagnetic energy emitted may be determined. Determination of the cumulative electromagnetic energy, calibration of the emitter, and/or independent determination may be carried out using equipment and procedures well known to those of ordinary skill in the art. For example, the power meters, energy sensors, and beam profilers available from Ophir-Spiricon LLC (North Logan, Utah, USA) may be used to determine the cumulative electromagnetic energy and/or calibrate the emitter.

Once the cumulative electromagnetic energy emitted has been determined, the emitter may be calibrated to emit a cumulative electromagnetic energy as desired above. The emitter may be calibrated to vary from a chosen cumulative electromagnetic energy by no more than, e.g., 1%, 0.1%, 0.01%, 0.001%, 0.0001%, or 0.00001%. Instead of calibrating the emitter, the length of the pulses, the number of pulses, and/or the wavelength of the electromagnetic energy may be altered to compensate for the actual cumulative electromagnetic energy emitted.

A system may comprise an electromagnetic energy emitter that emits electromagnetic energy at a desired amount of Joules per single/or cumulative pulses as identified above and a device designed to retain the cartilage structure in the orientation, shape, and/or location desired. The electromagnetic energy emitter may be calibrated and/or independently determined to emit the desired amount of Joules per single/or cumulative pulses.

The target cartilage may be part of a human or a non-human animal. Alternatively, the target cartilage may be present in culture.

The location, environment, and state of the cartilage structure may require different wavelengths, Hz, cumulative electromagnetic energy, number of pulses, Joules/pulse, and/or intervals between pulses. The above parameters may be varied so as to achieve the best cartilage remodeling and/or decreased side effects from the methods.

The device designed to retain the cartilage structure in the orientation, shape, and/or location may have its surface impregnated with various factors known to effect the growth and maturation of cartilage such as, but not limited to, IGF-I, TGF-beta1, BMP-7, PDGF-AB; and FGF-2.

The application of electromagnetic energy to the cartilage structure may comprise application to one or more of the surfaces of the cartilage structure. By way of non-limiting examples, application of electromagnetic energy to the ear may comprise lasing of both sides of the ear at the location to be stimulated, for example both sides of the entire helix and concha of the ear; application of electromagnetic energy to the nasal septum may comprise application to both surfaces of the septum; and application of electromagnetic energy to a spinal disc or meniscus of the knee may comprise application to all or some of the surfaces of these structures. The locations on a cartilage structure to be subject to the application of electromagnetic energy may include the entire structure or may be limited to particular portions of a cartilage structure in order to achieve a desired localization of chondrogenesis.

In addition, trauma may be applied to a cartilage structure or to the area around a cartilage structure in order to stimulate chondrogenesis in the cartilage structure. The trauma may be precisely localized to a particular area or may be diffuse. The locations on a cartilage structure to be subject to the trauma may include the entire structure or may be limited to particular portions of a cartilage structure in order to achieve a desired localization of chondrogenesis. The trauma may include but is not limited to blunt trauma, piercing trauma, and thermal trauma. Blunt trauma may include but is not limited to trauma caused by a physical impact or by shockwaves. Piercing trauma may include the application of one or more needles or microneedles to the cartilage structure or the area around the cartilage structure. Thermal trauma may be either cold trauma or heat trauma and may be applied by lowering or raising the temperature of the cartilage structure or the area surrounding it. Further, the temperature may be raised by imparting energy to the molecules of the cartilage structure or surrounding area by using electromagnetic radiation such as laser light or microwaves. Before, during, or after the application of the trauma, the cartilage structure may be fitted with a device designed to retain the cartilage structure in the orientation, shape, and/or location desired after the reforming of the cartilage structure.

It is intended that chondrogenesis may be stimulated in a cartilage structure by one or more of the methods described herein either serially or in parallel. Further, chondrogenesis may be stimulated by a single treatment or by multiple treatments by one or more of the method described herein in order to achieve the desired remodeling of the cartilage structure.

The device designed to retain the cartilage structure in the orientation, shape, and/or location may be placed on the cartilage structure and left in place until the cartilage structure is effectively reshaped by the device. The device may be left in place for a period of 3 to 6 weeks. The device may be worn continuously for the first 3 weeks and then only at night for an additional 3 weeks.

All elements described herein may be combined with any other element described herein. As such, all possible combinations of elements described herein, even if not explicitly set forth, are specifically included.

EXAMPLE 1

Laser-Assisted Cartilage Reshaping for Treating Ear Protrusions

Materials and Methods

Twenty-four subjects were treated by LACR. All subjects were informed of the purpose and possible outcomes of the study, signed forms of consent for the study, and agreed to clinical photography. There were 14 adults and 10 children. The subjects' mean age was 16.0 years (range=6-45 years). Pain was assessed by the subjects using a 4-point scale: none, slight, moderate, or severe For 21 subjects, the 1540 nm Er:YAG laser (Aramis, Quantel Derma GmbH, Erlangen, Germany) was set at 12 J/cm2 per pulse. The treatment consisted of seven stacked pulses (3 ms, 2 Hz, 84 J/cm2 cumulative fluence) applied using a 4-mm spot hand piece with integrated cooling (Koolburst, Quantel Derma GmbH, Erlangen, Germany) on both sides of the entire helix and concha. For the remaining three adults, the laser was set at a lower fluence of 10 J/cm2 per pulse for a total cumulative fluence of 70 J/cm2. The entire helix and concha were irradiated on both sides. Contact cooling made the treatment very tolerable, to the extent that topical anesthesia was not required (although local anesthetic certainly could have been used).

Twenty-four subjects underwent LACR of both ears using our 1.54-lm laser. Immediately after irradiation, a silicone elastomer (Hydro-C, Detax, Ettlingen, Germany) was inserted inside the helix to give it the desired shape. Three minutes later the elastomer hardened and a solid mold was obtained. The entire procedure took no more than 15-20 min per ear. Subjects were asked to wear this mold at all times for the first 3 weeks and then only at night for an additional 3 weeks. A non-steroidal anti-inflammatory drug (NSAID) was provided to all subjects for 3 days. Ears were checked at days 1, 30, 60, and 90 and photographs were taken. Clinical follow-up at 1 year was obtained via direct contact (n=22) or over the telephone (n=2).

Results

Postoperative follow-up was uneventful for all ears, except for six on which minor contact dermatitis developed probably because of inappropriate mold design. This did not require additional therapy and those subjects (4 children and 2 adults) stopped wearing the mold leading to incomplete shape correction. There were no cases of infection hematomas or skin necrosis. For the remaining 18 subjects (6 children and 9 adults) the expected ear reshaping was achieved (fluence=84 J/cm2) Table 1; in 3 adults, partial or incomplete reshaping was observed and correlated to a lower fluence (70 J/cm2). Those subjects were retreated at months at 84-J/cm2 fluence and all achieved suitable reshaping (Table 2). Again, no postoperative discomfort was reported.

TABLE 1

Our series of 48 reshaped ears using the 1540-nm laser on 24 patients

| N | Age (years) | Sex | Fluence (J/cm²) | Mold | Reshaping | Pain | Follow-up (months) |
|---|---|---|---|---|---|---|---|
| 1 | 6 | M | 84/84 | A/A | E/E | N/N | St/St |
| 2 | 6 | M | 84/84 | A/A | E/E | N/N | St/St |
| 3 | 7 | W | 84/84 | A/A | E/E | N/N | St/St |
| 4 | 7 | W | 84/84 | A/A | E/E | N/N | St/St |
| 5 | 6 | W | 84/84 | A/A | E/E | N/N | St/St |
| 6 | 8 | W | 84/84 | A/A | E/E | N/N | St/St |
| 7 | 19 | W | 84/84 | A/A | E/E | N/N | St/St |
| 8 | 24 | W | 84/84 | A/A | E/E | N/N | St/St |
| 9 | 22 | W | 84/84 | A/A | E/E | N/N | St/St |
| 10 | 20 | W | 84/84 | A/A | E/E | N/N | St/St |
| 11 | 16 | W | 84/84 | A/A | E/E | N/N | St/St |
| 12 | 18 | M | 84/84 | A/A | E/E | N/N | St/St |
| 13 | 22 | M | 84/84 | A/A | E/E | N/N | St/St |
| 14 | 22 | W | 84/84 | A/A | E/E | N/N | St/St |
| 15 | 45 | W | 84/84 | A/A | E/E | N/N | St/St |
| 16 | 24 | W | 84/84 | I/I | I/I | N/N | MR/MR |
| 17 | 22 | W | 84/84 | I/I | I/I | N/N | MR/MR |
| 18 | 8 | W | 84/84 | I/I | I/I | N/N | MR/MR |
| 19 | 6 | W | 84/84 | I/I | I/I | N/N | MR/MR |
| 20 | 6 | W | 84/84 | I/I | I/I | N/N | MR/MR |
| 21 | 8 | M | 84/84 | I/I | I/I | N/N | MR/MR |
| 22 | 22 | M | 70/70 | A/A | I/I | N/N | SeR/SeR |
| 23 | 18 | W | 70/70 | A/A | I/I | N/N | SeR/SeR |
| 24 | 22 | W | 70/70 | A/A | I/I | N/N | SeR/SeR |

M man,
W woman,
R/L right/left,
A appropriate,
I inappropriate,
E expected,
I incomplete,
N none,
S slight,
M moderate,
Se severe,
St stable,
SR slight recurrence,
MR moderate recurrence,
SeR severe recurrence

TABLE 2

Three patients underwent a second course of reshaping with a new fluence

| N | Age (years) | Sex | Fluence (J/cm²) | Mold | Reshaping | Pain | Follow-up (months) |
|---|---|---|---|---|---|---|---|
| 22 | 22 | M | 84/84 | A/A | E/E | N/N | St/St |
| 23 | 18 | W | 84/84 | A/A | E/E | N/N | St/St |
| 24 | 22 | W | 84/84 | A/A | E/E | N/N | St/St |

M male,
W woman,
A appropriate,
E expected,
N none,
St stable

EXAMPLE 2

Laser-Assisted Cartilage Reshaping for Treating Ear Protrusions

Materials and Methods

Groups of ten subjects are treated at different wavelengths, number of pulses, intervals separating pulses, and cumulative fluence levels by LACR. Each subject group receives the same treatment. Pain is assessed by the subjects using a 4-point scale: none, slight, moderate, or severe Lasers of 532, 755, 1064, 1320, 1540, 2940, and 10600 nm are obtained from Alma Lasers US (Buffalo Grove, Ill.). The lasers are set at 0.1, 0.5, 1, 3, 4, 6, 8, 10, 12, 14, 16, 18, 20, 22, 24, 26, 28, or 30 J/cm2 per pulse (with the length of the pulse chosen so as to determine the amount of energy per pulse) with an interval between pulses of 1, 10, 100, 200, 400, 600, 800, or 1000 nanoseconds or 10, 20, 40, 60, 80, 100, 200, 400, or 500 milliseconds. The treatment consists of 1, 2, 3, 4, 5, 6, 7, 8, 9, 10, 11, 12, 13, 14, or 15 stacked pulses to achieve 0.7, 3.5, 7, 21, 28, 42, 56, 70, 84, 98, 112, 126, 140, 154, 168, 182, 196, or 210 J/cm2 cumulative fluence using a 4-mm spot hand piece with integrated cooling on both sides of the entire helix and concha. The entire helix and concha are irradiated on both sides. Contact cooling makes the treatment very tolerable, to the extent that topical anesthesia is not required (although local anesthetic certainly could may be used).

Immediately after irradiation, the ear is placed in a device designed to retain the cartilage structure in the orientation, shape, and/or location. The entire procedure takes no more than 15-20 min per ear. Subjects are asked to wear the device at all times for the first 3 weeks and then only at night for an additional 3 weeks. A non-steroidal anti-inflammatory drug (NSAID) is provided to all subjects for 3 days. Ears are checked at days 1, 30, 60, and 90 and photographs are taken. Clinical follow-up at 1 year is obtained via direct contact or over the telephone (n=2).

Results

Postoperative follow-up is uneventful for all ears. The ear reshaping is achieved No postoperative discomfort is reported.

EXAMPLE 3

Electromagnetic Energy-Assisted Cartilage Reshaping for Treating Ear Protrusions Materials and Methods Groups of ten subjects are treated at different wavelengths, number of pulses, intervals separating pulses, and cumulative fluence levels by EMACR. Each subject group receives the same treatment. Pain is assessed by the subjects using a 4-point scale: none, slight, moderate, or severe Electromagnetic energy emitters of capable of emitting 0.001, 0.005, 0.01, 0.05, 0.1, 0.5, 1, 10, 20, 30, 40, and/or 50 MHz are obtained. The emitters are set at 0.1, 0.5, 1, 3, 4, 6, 8, 10, 12, 14, 16, 18, 20, 22, 24, 26, 28, or 30 J/cm2 per pulse (with the length of the pulse chosen so as to determine the amount of energy per pulse) with an interval between pulses of 1, 10, 100, 200, 400, 600, 800, or 1000 nanoseconds or 10, 20, 40, 60, 80, 100, 200, 400, or 500 milliseconds. The treatment consists of 1, 2, 3, 4, 5, 6, 7, 8, 9, 10, 11, 12, 13, 14, or 15 stacked pulses to achieve 0.7, 3.5, 7, 21, 28, 42, 56, 70, 84, 98, 112, 126, 140, 154, 168, 182, 196, or 210 J/cm2 cumulative fluence using a 4-mm spot hand piece on both sides of the entire helix and concha. The entire helix and concha are irradiated on both sides. The treatment is very tolerable, to the extent that topical anesthesia is not required (although local anesthetic certainly could may be used).

Immediately after irradiation, the ear is placed in a device designed to retain the cartilage structure in the orientation, shape, and/or location. The entire procedure takes no more than 15-20 min per ear. Subjects are asked to wear the device at all times for the first 3 weeks and then only at night for an additional 3 weeks. A non-steroidal anti-inflammatory drug (NSAID) is provided to all subjects for 3 days. Ears are checked at days 1, 30, 60, and 90 and photographs are taken. Clinical follow-up at 1 year is obtained via direct contact or over the telephone (n=2).

Results

Postoperative follow-up is uneventful for all ears. The ear reshaping is achieved No postoperative discomfort is reported.

EXAMPLE 4

Electromagnetic Energy-Assisted Cartilage Reshaping for Treating Ear Protrusions Materials and Methods Groups of ten subjects are treated at different wavelengths, number of pulses, intervals separating pulses, and cumulative fluence levels by EMACR. Each subject group receives the same treatment. Pain is assessed by the subjects using a 4-point scale: none, slight, moderate, or severe Electromagnetic energy emitters of capable of emitting 0.3, 0.6, 1, 10, 20, 40, 60, 80, 100, 120, 140, 160, 180, and/or 200 MHz are obtained. The emitters are set at 0.1, 0.5, 1, 3, 4, 6, 8, 10, 12, 14, 16, 18, 20, 22, 24, 26, 28, or 30 J/cm2 per pulse (with the length of the pulse chosen so as to determine the amount of energy per pulse) with an interval between pulses of 1, 10, 100, 200, 400, 600, 800, or 1000 nanoseconds or 10, 20, 40, 60, 80, 100, 200, 400, or 500 milliseconds. The treatment consists of 1, 2, 3, 4, 5, 6, 7, 8, 9, 10, 11, 12, 13, 14, or 15 stacked pulses to achieve 0.7, 3.5, 7, 21, 28, 42, 56, 70, 84, 98, 112, 126, 140, 154, 168, 182, 196, or 210 J/cm2 cumulative fluence using a 4-mm spot hand piece on both sides of the entire helix and concha. The entire helix and concha are irradiated on both sides. The treatment is very tolerable, to the extent that topical anesthesia is not required (although local anesthetic certainly could may be used).

Immediately after irradiation, the ear is placed in a device designed to retain the cartilage structure in the orientation, shape, and/or location. The entire procedure takes no more than 15-20 min per ear. Subjects are asked to wear the device at all times for the first 3 weeks and then only at night for an additional 3 weeks. A non-steroidal anti-inflammatory drug (NSAID) is provided to all subjects for 3 days. Ears are checked at days 1, 30, 60, and 90 and photographs are taken. Clinical follow-up at 1 year is obtained via direct contact or over the telephone (n=2).

Results

Postoperative follow-up is uneventful for all ears. The ear reshaping is achieved No postoperative discomfort is reported.

EXAMPLE 5

Trauma Assisted Cartilage Reshaping for Treating Ear Protrusions

Materials and Methods

Groups of ten subjects are treated with different forms of trauma. The traumas tested are blunt force, piecing with mirconeedles, heat trauma, and cold trauma. Each subject group receives the same treatment. Pain is assessed by the subjects using a 4-point scale: none, slight, moderate, or severe The entire helix and concha are traumatized on both sides. A topical anesthesia or local anesthetic is used to for the application of the trauma if necessary.

Immediately after trauma, the ear is placed in a device designed to retain the cartilage structure in the orientation, shape, and/or location. The entire procedure takes no more than 15-20 min per ear. Subjects are asked to wear the device at all times for the first 3 weeks and then only at night for an additional 3 weeks. A non-steroidal anti-inflammatory drug (NSAID) is provided to all subjects for 3 days. Ears are checked at days 1, 30, 60, and 90 and photographs are taken. Clinical follow-up at 1 year is obtained via direct contact or over the telephone (n=2).

Results

Postoperative follow-up is uneventful for all ears. The ear reshaping is achieved No postoperative discomfort is reported.

What is claimed is:

1. A method of shaping or reshaping a cartilage structure, the method comprising:
    treating the cartilage structure of a subject by applying electromagnetic energy to the cartilage structure with an emitter of electromagnetic energy calibrated to emit a total fluence of from 1 to 60 Joules of electromagnetic energy per square centimeter ($J/cm^2$) onto the cartilage structure within 1% of the calibrated total fluence so as to stimulate chondrogenesis in the cartilage structure; and
    fitting the treated cartilage structure with a device that retains the cartilage structure in a desired orientation, shape, and/or location so as to shape or reshape the cartilage structure.

2. The method according to claim 1, wherein the electromagnetic energy has a wavelength of from 250 nm to 1315 nm, 1325 nm to 1445 nm or 1455 nm to 1535 nm or 1540 nm at 11 $J/cm^2$ or less, or 1540 nm at 13 $J/cm^2$ or higher, or 1545 nm to 2095 nm or 2105 nm to 10600 nm or has a frequency of from 1000 Hz to 200 MHz.

3. The method according to claim 1, wherein the electromagnetic energy is applied to the cartilage structure in from 1 to 50 pulses.

4. The method according to claim 3, wherein each pulse is from 1 nanosecond to 1 second in length.

5. The method according to claim 3, wherein the interval between pulses is from 1 nanosecond to 1 second in length.

6. The method according to claim 3, wherein the electromagnetic energy applied per pulse is from 1.2 to 60 Joules.

7. The method according to claim 1, wherein the cartilage structure is selected from the group consisting of joints between bones, rib cage, ear, nose, elbow, knee, ankle, bronchial tubes, intervertebral discs, and nasal septum.

8. The method according to claim 7, wherein the cartilage structure is the ear.

9. The method according to claim 8, wherein the electromagnetic energy is applied to both sides of the cartilage structure.

10. The method according to claim 9, further wherein the device is fitted to the cartilage structure at all times for 3 weeks, then only at night for an additional 3 weeks.

11. The method according to claim 1, further comprising determining the total fluence emitted by the emitter of electromagnetic energy before treating the cartilage structure.

* * * * *